(12) United States Patent
Abbott et al.

(10) Patent No.: US 7,196,221 B2
(45) Date of Patent: Mar. 27, 2007

(54) IONIC LIQUIDS AND THEIR USE

(75) Inventors: Andrew P. Abbott, Leicester (GB); David L. Davies, Leicester (GB); Glen Capper, Exmouth (GB); Raymond K. Rasheed, Brampton (GB); Vasuki Tambyrajah, Dehiwala (LK)

(73) Assignee: Scionix Limited, London (GB)

( * ) Notice: Subject to any disclaimer, the term of this patent is extended or adjusted under 35 U.S.C. 154(b) by 218 days.

(21) Appl. No.: 10/381,059

(22) PCT Filed: Sep. 26, 2001

(86) PCT No.: PCT/GB01/04306

§ 371 (c)(1),
(2), (4) Date: Aug. 11, 2003

(87) PCT Pub. No.: WO02/26381

PCT Pub. Date: Apr. 4, 2002

(65) Prior Publication Data
US 2004/0054231 A1    Mar. 18, 2004

(30) Foreign Application Priority Data
Sep. 27, 2000  (GB) ................................ 0023708.1

(51) Int. Cl.
*C07C 211/00* (2006.01)
(52) U.S. Cl. ....................... 564/282; 564/291
(58) Field of Classification Search ............... 205/551, 205/552; 564/281, 282, 291, 292, 293, 296
See application file for complete search history.

(56) References Cited

U.S. PATENT DOCUMENTS 5,731,101 A * 3/1998 Sherif et al. ................ 429/102

6,573,405 B1 * 6/2003 Abbott et al. ............... 564/292

OTHER PUBLICATIONS

Saito, Shuji et al., "Complexes of urea and symmetrical tetraalkylammonium halides," J. Am. Chem. Soc., vol. 88 (No. 22), p. 5107-12, (1966).
O. Kristiansson et al., "Interaction between methanol and Cl-, Br-, I-, NO3-, CLO4-, SO3CF3- and PF6- Anions studied by FTIR Spectroscopy," Acta Chemica Scandinavica, vol. 51 (1997), p. 270-273, (1997).
Q Li et al., "Hydrogen-bonded Urea-Anion Host latticies.6. New inclusion compounds of urea with tetra-n-propylammonium halides," Acta Cryst., Intern'l Union of Cryst (Great Britain), vol. B54, 1998, p. 180-192, (1998).

(Continued)

*Primary Examiner*—Thurman Page
*Assistant Examiner*—Karl Puttlitz
(74) *Attorney, Agent, or Firm*—Bacon & Thomas, PLLC

(57) ABSTRACT

Ionic compounds having a freezing point of no more than 50° C., formed by the reaction of at least one amine salt of the formula $R^1R^2R^3R^4N^+X^-$ (I) with at least one hydrated salt, which is a chloride, nitrate, sulphate or acetate of Li, Mg, Ca, Cr, Mn, Fe, Co, Ni, Cu, Zn, Cd, Pb, Bi, La or Ce; wherein $R^1$, $R^2$ and $R^3$ are each independently a $C_1$ to $C_5$ alkyl or a $C_6$ to $C_{10}$ cycloalkyl group, or wherein $R^2$ and $R^3$ taken together represent a $C_4$ to $C_{10}$ alkylene group, thereby forming with the N atom of formula (I) a 5 to 11 membered heterocyclic ring, and wherein $R^4$ is hydrogen, or phenyl, or $C_1$ to $C_{12}$ alkyl or cycloalkyl group, optionally substituted with at least one group selected from OH, Cl, Br, F, I, phenyl, $NH_2$, CN, $NO_2$, $COOR_5$, CHO, $COR^5$ and $OR^5$, wherein $R^5$ is a $C_1$ to $C_{10}$ alkyl or cycloalkyl group, and $X^-$ is an anion capable of being complexed by the said hydrated salt. The compounds are useful as solvents, electrolytes, and catalysts, and have particular application in solvents/electrolytes for metal plating and electropolishing processes, in particular in chromium plating.

18 Claims, 2 Drawing Sheets

OTHER PUBLICATIONS

Figure 1:
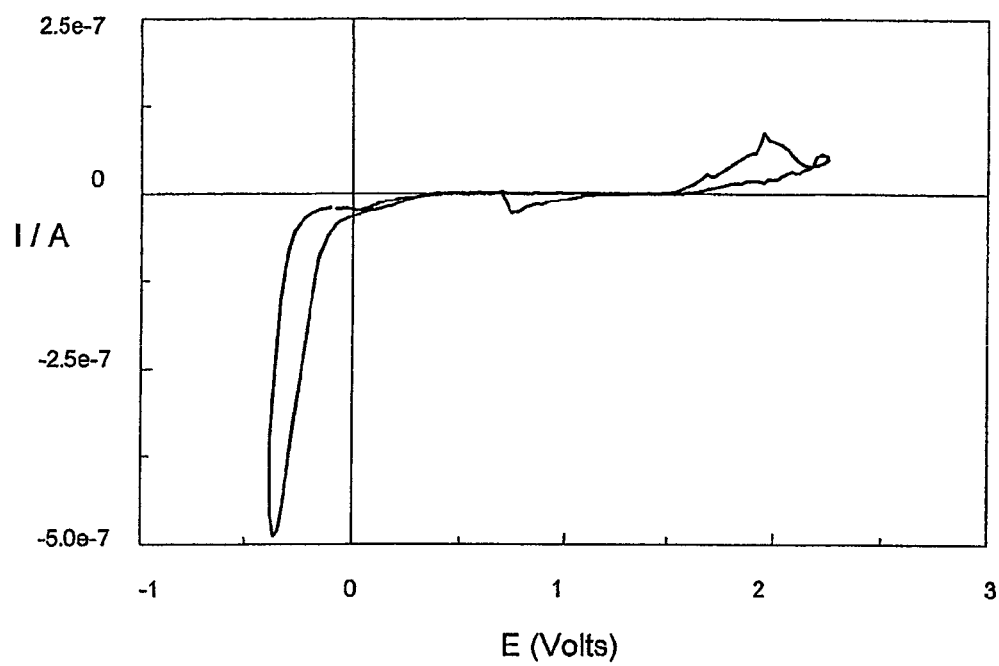

Q. Li, et al., "Tetra-n-butylammonium Chloride Thiourea (1/2) a layer type inclusion compound," Acta Crystallographica, Internat'l Union of Cryst (Great Britain), vol. C52, 1996, p. 2830-2832, (1996).

Mak, Thomas C.W., "Thiourea-halide lattices.1. Crystal Structures of (n-C4H9)4N+F-.3(NH2)2CS, (n-C4H9)3(CH3)N+X-.2(NH2)2CS (X=Cl, Br), and (n-C3H7)4N+I-.(NH2)2CS," Journ. of Inclusion Phenomena & Molecular Recognition in Chemistry, (Netherlands), p. 199-214, (1990).

Jahresbericht Ueber die Fortschritte der Chemie und Verwandter Teile Anderer Wissenschafter, pp. 531-547 (1857).

* cited by examiner

IONIC LIQUIDS AND THEIR USE

This invention relates to ionic compounds and methods for their preparation. In particular the invention relates to ionic compounds formed between hydrated metal salts and amine salts, which are liquid at low temperatures, and in particular which have a freezing point of 50° C. or less, and more preferably are liquid at or near to ambient temperature (20° C.)

There is much current interest in the field of ionic liquids. Such systems, which are examples of molten salts, have a number of interesting and useful chemical properties, and have utility, for example, as highly polar solvents for use in preparative chemistry, and as catalysts. They also have particular application in electrochemistry, for example in batteries, fuel cells, photovoltaic devices and electrodeposition processes, for example in baths for the electroplating of metals.

Ionic liquids have very low vapour pressure and thus, in contrast to many conventional solvents, produce virtually no hazardous vapours. They are therefore advantageous from a health, safety and environmental point of view.

One such system which has been known for many years is that formed from 1-ethyl-3-methylimidazolium chloride-aluminium chloride (EMIC-AlCl$_3$). This system is a thermally stable liquid between −100° C. and ca. 200° C., dependent on the molar ratio of EMIC to AlCl$_3$ utilised.

Such EMIC-AlCl$_3$ systems have been utilised extensively as solvents for various ionic reactions and as electrolytes, as described, for example in U.S. Pat. No. 5,525,567, FR-A-2611700, FR-A-2626572, WO95/21872, and EP-A-838447. There are a number of difficulties in utilising such compounds. These arise principally from their cost, and from their water sensitivity.

In recent years, other ionic compounds have been made which are liquid at relatively low temperatures. For example, U.S. Pat. No. 4,764,440 discloses low temperature molten compositions, formed by reacting, for example, trimethylphenylammonium chloride with aluminium trichloride. The resulting ionic compound has a low freezing point (around −75° C.), but suffers from the same water sensitivity as EMIC-AlCl$_3$, because of the presence of aluminium trichloride.

Proposals have been made to utilise other metal halides, in place of aluminium trichloride. For example, U.S. Pat. No. 5,731,101 discloses the use of iron and zinc halides as the anion portion of an ionic liquid composition. The cation portion is formed by an amine hydrohalide salt, of the formula R$_3$N.H.X (where X is halide). This reference indicates, however, that the aluminium compounds are preferred, and indeed contains comparative examples which indicate that it is not possible to substitute SnCl$_4$ for aluminium trichloride. Furthermore, it does not suggest the use of quaternary ammonium compounds as cations.

FR-A-2757850 (equivalent to U.S. Pat. No. 5,892,124) discloses liquid salts of the general formula Q$^+$A$^-$, wherein Q$^+$ represents quaternary ammonium or phosphonium, and A$^-$ represents various anions including tetrachloroaluminate and trichlorozincate. It is suggested that such compounds are useful as vehicles for carrying out Diels-Alder reactions.

F. N. Jones J. Org. Chem., 1967, 32, 1667–8 describes an ionic compound formed between Et$_4$N and SnCl$_3$ in a 1:1 molar ratio. The paper indicates that the solid and its solutions slowly decompose in air.

PCT/GB00/01090 describes liquid salts where the anion is a halide complex of zinc, iron or tin and the cation is chosen from certain specific quaternary ammonium compounds. Such salts are liquid at relatively low temperatures (i.e. below 60° C.), relatively inexpensive, and relatively water insensitive.

Because ionic liquids of this kind are generally water-sensitive, the conventional wisdom has been that all materials used in their preparation should be free of water, and in all of the above references the metals salts employed are anhydrous or dried prior to use.

Surprisingly, however, we have now found that by forming the anion of an ionic compound from a hydrated metal salt and the cation from certain specific amine salts, it is possible to produce compounds which are liquid at low temperatures (i.e. 50° C. and below), relatively inexpensive, and relatively water insensitive.

Accordingly, in a first aspect of the invention, there is provided an ionic compound having a freezing point of no more than 50° C., formed by the reaction of at least one amine salt of the formula $$R^1R^2R^3R^4N^+X^- \qquad (I)$$

with at least one hydrated salt, which is a chloride, nitrate, sulphate or acetate of Li, Mg, Ca, Cr, Mn, Fe, Co, Ni, Cu, Zn, Cd, Sn, Pb, Bi, La or Ce; wherein R$^1$, R$^2$ and R$^3$ are each independently a C$_1$ to C$_5$ alkyl or a C$_6$ to C$_{10}$ cycloalkyl group, or wherein R$^2$ and R$^3$ taken together represent a C$_4$ to C$_{10}$ alkylene group, thereby forming with the N atom of formula I a 5 to 11 membered heterocyclic ring, and wherein R$^4$ is hydrogen, or phenyl, or a C$_1$ to C$_{12}$ alkyl or cycloalkyl group, optionally substituted with at least one group selected from OH, Cl, Br, F, I, phenyl, NH$_2$, CN, NO$_2$, COOR$^5$, CHO, COR$^5$ and OR$^5$, wherein R$^5$ is a C$_1$ to C$_{10}$ alkyl or cycloalkyl group, and X$^-$ is an anion capable of being complexed by the said hydrated salt.

In the amine salts (I) used in the preparation preferably R$^1$, R$^2$, R$^3$, are independently C$_1$ to C$_5$ alkyl or cycloalkyl groups, and more preferably R$^1$, R$^2$, R$^3$, are independently methyl, ethyl or butyl. It is particularly preferred that R$^1$, R$^2$, R$^3$, are each methyl, R$^1$, R$^2$, R$^3$, are each ethyl, or R$^1$, R$^2$, R$^3$, are each butyl.

R$^4$ is preferably a C$_1$ to C$_{10}$ alkyl or a cycloalkyl group, substituted with at least one group selected from OH, Cl, Br, F, I, phenyl, NH$_2$, CN, NO$_2$, COOR$^5$, CHO, COR$^5$ and OR$^5$. The counterion X$^-$ of compound (I) is preferably a halide, for example bromide or chloride. Specific examples of amine salts which have been found to be suitable are choline chloride, tetraethylammonium chloride, triethylammonium chloride and benzyltrimethylammonium chloride.

The hydrated metal salt is preferably one of ZnCl$_2$.2H$_2$O, CaCl$_2$.6H$_2$O, MgCl$_2$.6H$_2$O, CrCl$_3$.6H$_2$O, CoCl$_2$.6H$_2$O, LaCl$_3$.6H$_2$O, CuCl$_2$.2H$_2$O, LiCl.5H$_2$O, Ca(NO$_3$)$_2$.4H$_2$O, Cr(NO$_3$)$_3$.9H$_2$O, Mn(NO$_3$)$_2$.4H$_2$O, Fe(NO$_3$)$_3$.9H$_2$O, Co(NO$_3$)$_2$.6H$_2$O, Ni(NO$_3$)$_2$.6H$_2$O, Cu(NO$_3$)$_2$.3H$_2$O, Li(NO$_3$).H$_2$O, Mg(NO$_3$)$_2$.6H$_2$O, La(NO$_3$)$_3$.6H$_2$O, Cd(NO$_3$)$_2$.4H$_2$O, Ce(NO$_3$)$_3$.6H$_2$O, Bi(NO$_3$)$_3$.5H$_2$O, Zn(NO$_3$)$_2$.4H$_2$O, Cd(OAc)$_2$.2H$_2$O, Pb(OAc)$_2$.3H$_2$O, or Cr$_2$(SO$_4$)3.15H$_2$O, and it is generally found that the most favourable freezing point is obtained when the molar ratio of the amine salt to the hydrated metal salt is from 1:1 to 1:2.5, more preferably around 1:2.

The ionic compounds according to the invention may be prepared simply by mixing together the amine salt (I), and the hydrated metal salt. The reaction is generally endothermic, and is usually carried out by heating, for example to a temperature of 100° C. or more. No additional solvent is generally employed.

The ionic compounds according to the invention find particular application where a polar but non-aqueous solvent is required. In particular, they may be employed as inert media, for dissolving ionic species such as transition metal complexes and, either alone or after complexing with other metal ions, as catalysts (particularly for cycloaddition reactions), or as chemical reagents.

They may be utilised for example as electrolytes in electrochemical devices such as batteries or fuel cells, in photovoltaic or electrochromic devices, and as solvents for electrochemical reactions, in particular for electrochemical deposition or electro-refining. Electrodeposition from an ionic liquid containing a mixture of hydrated metal salts may be preferred. In particular, compounds of the invention which incorporate chromium (III) ions have been found highly advantageous as solvents in the electroplating of chromium. In such processes using the ionic compounds according to the invention the addition of brightening agents and the use of potential cycling have been found to improve the appearance of the coatings obtained. Conventional chromium plating baths require the use of strong acids, which poses significant disposal problems, and the use of the compounds of the invention enables such disposal difficulties to be minimised or eliminated.

The ionic compounds according to the invention also find application in electropolishing. For example, both aluminium and stainless steel can be polished using compounds according to the invention. Stainless steels form the largest commercial application for electropolishing and traditionally polishing baths contain mixtures based on concentrated sulphuric and phosphoric acid. These are highly toxic, and corrosive and prone to form toxic and corrosive "mists" during electropolishing, as a result of prodigious gas evolution due to the high current densities used. A major advantage of the preferred electropolishing processes according to the invention is that they are generally more environmentally friendly compared with the conventional methods. Additional advantages offered are that they can be performed at room temperature and can operate with lower power consumption, whilst providing bright reflective finishes comparable to traditional techniques. An additional advantage of the materials in accordance with the invention is that when they are used in electrolytic baths, in particular plating or electropolishing baths, hydrogen evolution is significantly reduced, as compared with the acidic baths conventionally employed. This has a number of important consequences. First it results in very high current efficiency. Current efficiencies as high as 90% or more can be obtained in favourable circumstances. Reduced hydrogen evolution is also advantageous from the safety standpoint and reduces significantly the amount of hydrogen embrittlement that occurs in the substrate material during the electrochemical process. It also results in plated materials having an improved surface finish, with greatly diminished micro-cracking than is the case with electroplatings produced by conventional methods. This in turn can improve the corrosion resistance of the coatings, and/or allow the use of coatings which are thinner, and yet provide comparable corrosion resistance to that of conventional coatings, and thus are cheaper to produce, less consumptive of raw materials, and more environmentally friendly.

In the following Examples, The freezing points of the hydrated salt mixtures were all determined to be below 50° C. The conductivities of the hydrated salt mixtures were measured to determine their ionic nature. In each case, the conductivity was at least 10 microsiemens $cm^{-1}$ at 10° C. above the freezing point of the material.

A number of preferred embodiments of the invention are illustrated in the following Examples, and with reference to the accompanying Examples, in which:—

Figure 2:
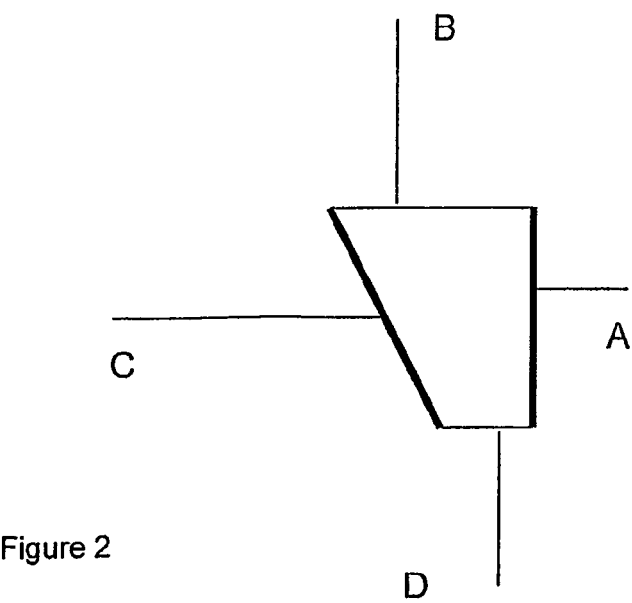

FIG. 1 is a cyclic voltammagram of an ionic liquid formed from a 2:1 molar ratio of chromium (III) chloride hexahydrate and choline chloride;

FIG. 2 ia a schematic diagram of Hull cell used for chromium deposition; and

Figure 3:
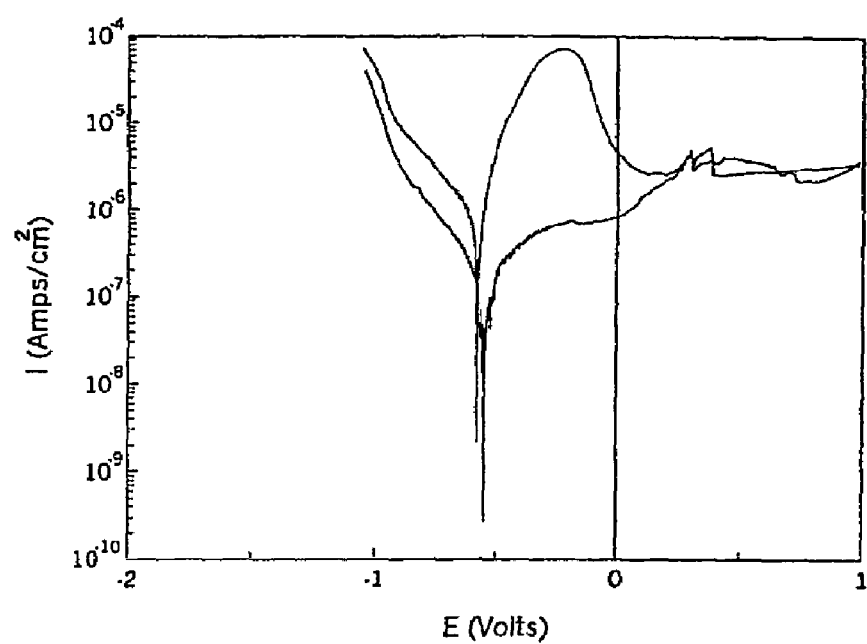

FIG. 3 is a voltage/current plot obtained in a chromium plating experiment using an ionic liquid as used in FIG. 1.

EXAMPLE 1

A quaternary amine salt (choline chloride 1.40 g (0.01 mole)) was added to a hydrated metal salt ($CrCl_3.6H_2O$ 5.33 g (0.02 mole)) in a laboratory test tube. The mixture was heated to a temperature of 120° C. for a period of 20 minutes. The product is a liquid which is initially purple in colour at 120° C. and a green liquid at 60° C.

EXAMPLES 2 TO 15

Example 1 was repeated, using various hydrated chlorides as shown in Table 1, in a molar ratio of 1:2 (Amine salt:$MCl_x.yH_2O$) as in Example 1 or in a molar ratio of 1:1. In each case, an ionic compound was prepared which had a freezing point of no more than 50° C. Freezing points (f.p.) are shown in Table 1.

TABLE 1

| $MCl_x$•$yH_2O$: Choline Chloride (2:1) | | | $MCl_x$•$yH_2O$: Choline Chloride (1:1) | | |
|---|---|---|---|---|---|
| Example | Hydrated Salt | f · p/ ° C. | Example | Hydrated Salt | f · p/ ° C. |
| 1 | $CrCl_3$•$6H_2O$ | 4 | 9 | $MgCl_2$•$6H_2O$ | 16 |
| 2 | $CaCl_2$•$6H_2O$ | 5 | 10 | LiCl•$5H_2O$ | 50 |
| 3 | $MgCl_2$•$6H_2O$ | 10 | 11 | $CrCl_3$•$6H_2O$ | 10 |
| 4 | $CoCl_2$•$6H_2O$ | 16 | 12 | $LaCl_3$•$6H_2O$ | 14 |
| 5 | $LaCl_3$•$6H_2O$ | 6 | 13 | $CoCl_2$•$6H_2O$ | 20 |
| 6 | $CuCl_2$•$2H_2O$ | 48 | 14 | $CuCl_2$•$2H_2O$ | 34 |
| 8 | $ZnCl_2$•$2H_2O$ | 20 | 15 | $ZnCl_2$•$2H_2O$ | 20 |

EXAMPLES 16 TO 40

Example 1 was repeated, using various hydrated nitrates as shown in Table 2, in a molar ratio of 1:2 (Amine salt:$MCl_x.yH_2O$) as in Example 1 or in a molar ratio of 1:1. In each case, an ionic compound was prepared which had a freezing point of not higher than 50° C.

TABLE 2

| $M(NO_3)_x$•$yH_2O$: Choline Chloride (2:1) | | $M(NO_3)_x$•$yH_2O$: Choline Chloride (1:1) | |
|---|---|---|---|
| Example | Hydrated Salt | Example | Hydrated Salt |
| 16 | $Ca(NO_3)_2$•$4H_2O$ | 30 | $Ca(NO_3)_2$•$4H_2O$ |
| 17 | $Cr(NO_3)_3$•$9H_2O$ | 31 | $Mn(NO_3)_2$•$4H_2O$ |
| 18 | $Mn(NO_3)_2$•$4H_2O$ | 32 | $Co(NO_3)_2$•$6H_2O$ |
| 19 | $Fe(NO_3)_3$•$9H_2O$ | 33 | $Ni(NO_3)_2$•$6H_2O$ |
| 20 | $Co(NO_3)_2$•$6H_2O$ | 34 | $Cu(NO_3)_2$•$3H_2O$ |
| 21 | $Ni(NO_3)_2$•$6H_2O$ | 35 | $Li(NO_3)$•$H_2O$ |
| 22 | $Cu(NO_3)_2$•$3H_2O$ | 36 | $Mg(NO_3)_2$•$6H_2O$ |
| 23 | $Li(NO_3)$•$H_2O$ | 37 | $La(NO_3)_3$•$6H_2O$ |
| 24 | $Mg(NO_3)_2$•$6H_2O$ | 38 | $Cd(NO_3)_2$•$4H_2O$ |
| 25 | $La(NO_3)_3$•$6H_2O$ | 39 | $Ce(NO_3)_3$•$6H_2O$ |
| 26 | $Cd(NO_3)_2$•$4H_2O$ | 40 | $Bi(NO_3)_3$•$5H_2O$ |

TABLE 2-continued

| M(NO$_3$)$_x$·yH$_2$O: Choline Chloride (2:1) | | M(NO$_3$)$_x$·yH$_2$O: Choline Chloride (1:1) | |
|---|---|---|---|
| Example | Hydrated Salt | Example | Hydrated Salt |
| 27 | Ce(NO$_3$)$_3$·6H$_2$O | | |
| 28 | Bi(NO$_3$)$_3$·5H$_2$O | | |
| 29 | Zn(NO$_3$)$_2$·4H$_2$O | | |

EXAMPLES 41 TO 46

Example 1 was repeated, using various hydrated salts (except chlorides or nitrates) as shown in Table 3, in a molar ratio of 1:2 (Amine salt:MCl$_x$·yH$_2$O) as in Example 1 or in a molar ratio of 1:1. In each case, an ionic compound was prepared which had a freezing point of not higher than 50° C.

TABLE 3

| MY$_x$·yH$_2$O: Choline Chloride (2:1) | | MY$_x$·yH$_2$O: Choline Chloride (1:1) | |
|---|---|---|---|
| Example | Hydrated Salt | Example | Hydrated Salt |
| 41 | Cd(CH$_3$COO)$_2$·2H$_2$O | 44 | Cd(CH$_3$COO)$_2$·2H$_2$O |
| 42 | Pb(CH$_3$COO)$_2$·3H$_2$O | 45 | Pb(CH$_3$COO)$_2$·3H$_2$O |
| 43 | Cr$_2$(SO$_4$)$_3$·15H$_2$O | 46 | Cr$_2$(SO$_4$)$_3$·15H$_2$O |

EXAMPLES 47 TO 49

Example 1 was repeated, using as the amine salt tetraethylammonium chloride (47), triethylammonium chloride (48) and benzyltrimethylammonium chloride (49), in molar proportion 1:2 (Amine salt:MCl$_x$·yH$_2$O).

EXAMPLE 50

Physical, Electrochemical and Chemical Properties of 2:1 chromium (III) chloride hexahydrate-choline chloride Hydrated Salt Mixture Below 80° C. the chromium hydrated salt mixture is a clear dark green liquid and at moderate temperatures (40° C. to 60° C.) it is reasonably fluid. When heated to 80° C. the liquid turns purple. It is thought that the colour change is due to the loss of water from the Cr coordination sphere.

The conductivity of the chromium hydrated salt mixture varies with temperature. The temperature dependence was determined with the aid of a Jenway 4071 Conductivity Meter and Conductivity Probe. The probe was immersed in 2:1 chromium (III) chloride hexahydrate-choline chloride contained in a sample tube which in turn was suspended in an oil bath. The hydrated salt mixture was heated to different temperatures and the resulting conductivity values were recorded. The results obtained are shown in Table 4.

TABLE 4

| Temperature/° C. | Conductivity/mScm$^{-1}$ |
|---|---|
| 20.4 | 0.12 |
| 35.6 | 1.34 |
| 42.1 | 2.17 |
| 54.3 | 3.41 |
| 63.3 | 4.02 |
| 69.8 | 5.08 |
| 73.4 | 5.41 |
| 84.9 | 6.92 |
| 96.4 | 8.21 |

The chemical composition of the 2:1 chromium (III) chloride hexahydrate-choline chloride hydrated salt mixture was studied using mass spectrometry. The instrument used in this study was a Kratos Concept Sector Mass Spectrometer equipped with negative ion fast ion bombardment (FAB). FAB mass spectra were obtained by introducing a small amount of chromium hydrated salt mixture into the sample chamber and bombarding it with Xe atoms accelerated by a potential of 4 kV. The resulting spectra revealed evidence for the existence of [CrCl$_4$]$^-$ (m/z 194).

EXAMPLE 51

Chromium Electrodeposition

A 2:1 chromium (III) chloride hexahydrate-choline chloride hydrated salt mixture (~5 ml) was prepared, by the method of Example 1, and poured into an electrochemical cell held in an oil bath at 60° C. Voltammetry was performed using a 10 μm diameter platinum working electrode, a Pt wire counter-electrode and a chromium rod immersed in the chromium hydrated salt mixture as the reference electrode. A PGSTAT20 Potentiostat controlled by GPES software was used to carry out the cyclic voltammetry. The results of this study are shown in FIG. 1.

The effect of current density on chromium deposition was investigated using a Hull cell. The structure of the Hull cell enables the deposition of a metal at a range of current densities to be obtained on a single cathode. A schematic diagram of the Hull cell employed is shown in FIG. 2.

To demonstrate chromium deposition a chromium (III) chloride-choline chloride hydrated salt mixture was prepared, by the method of Example 1, and poured into a Hull cell as shown in FIG. 2, having dimensions A=4.0 cm
B=5.0 cm
C=5.3 cm
D=1.3 cm to a depth of approximately 1 cm.

The cathodic plate (substrate), 50 mm by 42 mm and 0.5 mm thick, was gently abraded with glass paper, cleaned with acetone and flame annealed. The cathodic plate was then placed inside the Hull cell along edge C. The anodic plate, 40 mm by 40 mm and 1 mm thick, was cleaned in a similar way and then placed inside the Hull cell along edge A. The Hull cell was then suspended in a water bath set to a temperature so as to maintain the chromium hydrated salt mixture at 60° C. Chromium deposition was achieved by connecting the metal substrate and the counter-electrode plates to the negative and positive terminals respectively of a Thurlby Thander power pack. In order accurately to monitor the current flowing in the circuit, an ISO-TECH IDM 66 Digital Voltmeter was connected in series. Chromium was plated onto nickel, mild steel and aluminium substrates. In all of the experiments the deposition time was 2 hours, after which time the substrates were removed from the Hull cell, washed with acetone and dried. The effects of hydrated salt mixture composition and anode material (copper, nickel, graphite or aluminium) were investigated. The results obtained are described in the following sections.

Chromium Deposition onto Nickel

Using a copper counter-electrode and a hydrated salt mixture composition of $CrCl_3.6H_2O$-choline chloride (2:1) a thick dark grey/green homogeneous deposit was obtained with current densities between 0.39 and 0.25 $mAcm^{-2}$. A thinner greyer deposit was obtained with current densities between 0.25 and 0.19 $mAcm^{-2}$. Below 0.19 $mAcm^{-2}$ the chromium deposit was faint and non-homogeneous. Numerous brightening agents were added to the hydrated salt mixtures to improve the surface finish of the electrodeposited material. The addition of thiourea (0.75 wt %) to the electrolyte produced a fainter non-homogenous deposit. Hydrogen was also produced at the cathodic surface and this had a detrimental effect on the quality of the chromium deposit. The addition of saccharin (0.75 wt %) had no significant effect on the appearance of the deposited chromium, however it should be noted that saccharin only partially dissolves in the electrolyte. Similar chromium deposits were obtained from the $CrCl_3.6H_2O$-choline chloride (2:1) electrolyte when nickel or graphite were used as an anode in place of copper.

Chromium Deposition onto Mild Steel

Chromium was successfully electroplated onto mild steel and in general the deposits were thick and adherent. The major advantage of the process described in this report is that pre-treatment of mild steel substrates is not required. Using a nickel anode and an electrolyte composition of $CrCl_3.6H_2O$-choline chloride (2:1) a thick dark green/grey deposit was obtained with current densities between 0.39 and 0.24 $mAcm^{-2}$. A paler blue/grey deposit was obtained with current densities between 0.24 and 0.21 $mAcm^{-2}$. Between 0.21 and 0.18 $mAcm^{-2}$ the deposited chromium film was faint and non-homogenous. When the nickel counter-electrode was replaced with either carbon or aluminium the chromium deposits obtained were fainter, thinner and less homogenous. Darker chromium deposits were obtained when a small amount of the $CrCl_3.6H_2O$ in the electrolyte was substituted by LiCl or $MgCl_2.6H_2O$ to give $CrCl_3.6H_2O$-LiCl-choline chloride (1.5:0.5:1) and $CrCl_3.6H_2O$-$MgCl_2.6H_2O$-choline chloride (1.8:0.2:1) respectively. With a nickel counter-electrode and a current density between 0.33 and 0.21 $mAcm^{-2}$ a smooth dark grey/brown adherent chromium deposit was obtained from the $CrCl_3.6H_2O$-LiCl-choline chloride (1.5:0.5:1) electrolyte.

Several materials were tested as brighteners in the above experiment. In each experiment, a nickel anode was used. Some of the materials tested were immiscible with the electrolyte (vanillin—3.58 wt % and allyl urea—4.11 wt %) and had no effect on chromium electrodeposition. Nicotinic acid (4.11 wt %) and citric acid (1.82 wt %) dissolved in the electrolyte and the resulting chromium deposits were slightly paler—however these materials led to hydrogen evolution at the substrate surface which in turn reduced the homogeneity of the electrodeposited chromium film. Gelatin (3.58 wt %) only partially dissolved in the $CrCl_3.6H_2O$-choline chloride (2:1) electrolyte at 60° C. and after approximately 10 minutes it caused the electrolyte to thicken and become less conductive. The chromium film obtained was predominantly green/grey but in places it was non-adherent. A similar deposit was obtained when 2-mercaptobenzothiazole (2.34 wt %) was tested as a brightener.

We have found that the presence of specific additives, not generally recognised as brighteners, in 2:1 chromium (III) chloride hexahydrate-choline chloride can significantly brighten the electrodeposit. For example when 10% of choline chloride is replaced by tetraethylammonium fluoride dihydrate or tetramethylammonium hydroxide pentahydrate thin semi-bright pale blue chromium deposits can be obtained. Approximately 6 ml of 2:1 chromium (III) chloride hexahydrate-[choline chloride (90%) tetraethylammonium fluoride dihydrate (10%)] was prepared by combining the reactants in a beaker and heating at 80° C. The green liquid was poured into an electrochemical cell (internal diameter of 23 mm) held in an oil bath at 60° C. Mild steel (50 mm by 10 mm and 1 mm thick), cleaned in the usual way, was fixed to the inside edge of the cell opposite a nickel counter electrode. The mild steel plate and counter-electrode were then connected to the negative and positive terminals respectively of a Thurlby Thander power pack. Using current densities between 8 and 16 $mAcm^{-2}$ and deposition times between 10 and 30 minutes semi-bright chromium deposits were obtained. The procedure was repeated using approximately 6 ml of 2:1 chromium (III) chloride hexahydrate-[choline chloride (90%) tetramethylammonium hydroxide pentahydrate (10%)]. With a current density of 2 $mAcm^{-2}$ thin pale blue semi-bright homogenous chromium deposits were obtained after 30 minutes.

Similar electrodeposits were obtained when either potassium dichromate (1.74 wt %) or potassium permanganate (1.41 wt %) were added to the 2:1 chromium chloride hexahydrate-choline chloride hydrated salt mixture. Using the experimental set up described above, a current density of 2 $mAcm^{-2}$ and a deposition time of 30 minutes, homogenous semi-bright thin films of chromium were plated onto mild steel.

Chromium Deposition onto Aluminium

The $CrCl_3.6H_2O$-choline chloride (2:1) electrolyte could also be used to electrodeposit chromium onto an untreated aluminium surface. With a nickel counter-electrode and a current density between 0.47 and 0.30 $mAcm^{-2}$ a grey/blue deposit was obtained. Between 0.30 and 0.25 $mAcm^{-2}$ the deposit was slightly paler and greyer and between 0.25 and 0.22 $mAcm^{-2}$ the chromium film became non-homogenous. As was the case with electroplating chromium onto mild steel, darker deposits were obtained when LiCl was incorporated into the electrolyte. With the electrolyte composition $CrCl_3.6H_2O$-LiCl-choline chloride (2.25:0.75:1) and a current density between 0.47 and 0.28 $mAcm^{-2}$ a thick black homogenous deposit was obtained. Between 0.28 and 0.22 $mAcm^{-2}$ the deposit was dark grey and less homogenous. Below 0.22 $mAcm^{-2}$ chromium was not electroplated onto the aluminium surface.

EXAMPLE 52

Potentiodynamic Electroplating Conditions

The above Examples show that chromium can be electroplated from the $CrCl_3.6H_2O$-choline chloride (2:1) electrolyte onto nickel, mild steel and aluminium using potentiostatic conditions. The deposits obtained are thick, adherent and homogenous, but in general they lack brightness. The surface finish of the chromium deposits was improved using a potentiodynamic technique rather than a potentiostatic technique. The potential cycling regime was studied and optimised such that semi-bright chromium could be obtained. For these studies potentiodynamic conditions were used with two parallel electrodes which were 17 mm apart. The cell has a depth of 3.5 cm.

For each experiment a Cr(III)-choline chloride hydrated salt mixture was prepared, by the method of Example 1, and poured into the cell to a depth of approximately 2.5 cm. The electrodes, 52×42×0.5 mm thick, were prepared by the same method reported above. The potential limits and the potential sweep rates for the potentiodynamic studies were controlled using a PGSTAT20 Potentiostat. The potentiostat was used in a 'two electrode' configuration. Chromium was plated onto mild steel and a variety of anode materials were tested.

Using a $CrCl_3.6H_2O$-choline chloride (1.8:1) mixture with a copper anode and a potential cycling range of 0V to −1.5 V at 20 mVs$^{-1}$ a semi-bright silver/blue chromium deposit was obtained after 28 cycles. When the cycling range was increased to 0 V to −1.8 V a slightly thicker silver grey deposit was obtained. A further increase in the cycling range to 0V to −2.1V produced a greyer deposit. Semi-bright silver/blue chromium films were also obtained from the $CrCl_3.6H_2O$-choline chloride (1.8:1) electrolyte with nickel and lead counter electrodes. Silver/grey deposits were obtained when aluminium, stainless steel and zinc were used as the anode material. When mild steel or graphite were used as anodes the resulting chromium films were faint and non-homogenous.

Post-Treatment and Corrosion Studies

The corrosion resistance afforded by chromium plated onto mild steel using potentiodynamic conditions was assessed by holding the samples approximately 5 cm above a boiling 10 wt % salt solution. The unprotected regions began to rust after approximately 40 minutes and soon after rust spots appeared in the chromium films. EDX analysis was performed on newly plated chromium films and the analyses showed that chloride, from the electrolyte, had been incorporated into the metal deposit. It is thought that the presence of chloride reduces the crystallinity of the metal deposit and in the presence of moisture these aid the breakdown of passivating films on the chromium surface. In order to improve the corrosion resistance of the chromium films an additional post-treatment step was performed. This involved dipping the chromium coated sample, together with a counter electrode, into 0.1M $KNO_3$ and applying a potential difference of 1.5V for 30 minutes thus allowing the chloride ions to be removed and the surface to be passivated. Chromium films prepared from the $CrCl_3.6H_2O$-choline chloride (1.8:1) electrolyte with copper, nickel, lead or aluminium counter electrodes and a potential cycling range of 0 to −1.5 V were treated in this manner. The corrosion protection offered by these chromium deposits was excellent. The aforementioned corrosion test was repeated with various samples and there was no obvious sign of corrosion after 24 hours—only slight staining of the chromium films occurred.

An electrochemical technique was also used to determine the effectiveness of chromium plating. A 1 mm diameter iron electrode was polished with alumina paste down to 0.3 μm. Together with a polished platinum electrode and a saturated calomel reference electrode (SCE) the iron electrode was immersed in 50 ml of 0.1 M potassium nitrate solution. The potential of the iron electrode was swept from −1 V to 1 V versus SCE at 20 mVs$^{-1}$. The scan (curve A) including the current arising from iron oxidation is shown in FIG. 3.

The iron electrode was then cleaned, dried and immersed in 2:1 chromium (III) chloride hexahydrate-choline chloride hydrated salt mixture contained in a boiling tube. Using a platinum electrode as a counter and a chromium rod as a reference, chromium was deposited onto the iron at −0.25V versus chromium for 60 minutes. The deposition was performed at 60° C. The iron electrode was then removed from the hydrated salt mixture, washed with acetone, dried and re-immersed in 0.1M potassium nitrate solution. As before the potential of the iron electrode was swept from −1 V to 1 V versus SCE at 20 mVs$^{-1}$ (curve B). It can clearly be seen that chromium plating has reduced the corrosion current by approximately 250 times.

EXAMPLE 53

Cobalt Electrodeposition

A 2:1 cobalt (II) chloride hexahydrate-choline chloride hydrated salt mixture (~5 ml) was prepared, by the method of Example 1, and poured into an electrochemical cell held in an oil bath at 60° C. Voltammetry was performed using a platinum microelectrode (10 μm diameter), a platinum counter-electrode and a cobalt reference electrode. An Autolab PGSTAT12 Potentiostat controlled by GPES software was used to carry out the cyclic voltammetry.

To demonstrate cobalt deposition a 2:1 cobalt (II) chloride hexahydrate-choline chloride hydrated salt mixture (~7 ml) was prepared and poured into an electrochemical cell (23 mm internal diameter) held in an oil bath at 60° C. A mild steel plate, 50 mm by 10 mm and 1 mm thick, was gently abraded with glass paper, cleaned with acetone and flame annealed. The mild steel plate was then fixed to the inside edge of the cell. A nickel plate of equal dimensions was cleaned in a similar way and also fixed to the inside edge of the cell opposite the mild steel plate. Cobalt deposition was achieved by connecting the mild steel and nickel plates to the negative and positive terminals respectively of a Thurlby Thander power pack respectively. A potential was applied and adjusted so as to maintain a current density of 2 mAcm$^{-2}$ for 30 minutes. An ISO-TECH IDM 66 Digital Voltmeter connected in series was used to monitor the current. After 30 minutes the mild steel plate was removed from the cell, rinsed with acetone and dried. With a current density of 2 mAcm$^{-2}$ a semi-bright grey/brown homogenous deposit was obtained.

EXAMPLE 54

Silver Deposition

A 2:1 tin (II) chloride dihydrate-choline chloride hydrated salt mixture (6.94 g) was prepared, by the method of example 1, and poured into an electrochemical cell held in an oil bath at 60° C. Silver chloride (0.3% wt)) was added to the clear colourless melt and dissolved. Voltammetry was performed using a platinum microelectrode (10 μm diameter), a platinum counter-electrode and a tin reference electrode. An Autolab PGSTAT12 Potentiostat controlled by GPES software was used to carry out the cyclic voltammetry. This technique could be used as the basis for an electrochromic device where a layer of silver was deposited on a glass window.

To demonstrate silver deposition ITO glass (65 mm by 13 mm) and a nickel counter-electrode (50 mm by 10 mm) were fixed to the inside edge of the electrochemical cell opposite each other. Tin wire was dipped into the ionic liquid and using the Autolab PGSTAT12 Potentiostat silver was plated onto the ITO glass at 0.25 V versus tin. After 30 minutes a dull grey semi-transparent film was obtained.

Silver has also been deposited from 2:1 lithium nitrate hydrate-choline chloride. The hydrated salt mixture was prepared, by the method of example 1, poured into an electrochemical cell to which silver chloride (0.3% wt) was added and dissolved, and the resulting liquid was subjected to cyclic voltammetry using a platinum microelectrode and a silver wire as a reference electrode. To demonstrate silver deposition indium-tin oxide (ITO) glass (65 mm by 13 mm) and a nickel counter-electrode (50 mm by 10 mm) were fixed to the inside edge of the electrochemical cell opposite each other and connected to the negative and positive terminals respectively of a Thurlby Thander power pack. A potential difference of 2 volts was applied and after 20 minutes a dull grey semi-transparent film was obtained.

EXAMPLE 55

Aluminium Electropolishing

An ionic liquid was prepared from a 2:1 mixture of zinc (II) nitrate tetrahydrate and choline chloride (~5 ml), by the method of Example 1. The material was cooled to 20° C. and poured into an electrochemical cell. An aluminium electrode (52 mm by 7 mm and 1 mm thick) was cleaned, degreased and fixed to the inside edge of the electrochemical cell. A carbon counter-electrode was cleaned with a cloth moistened with acetone and fixed to the inside edge of the electrochemical cell opposite the aluminium electrode. The aluminium and carbon electrodes were connected to the positive and negative terminals respectively of a Thurlby Thander power pack. Various potentials were applied for 6 minutes and the initial current densities at the aluminium electrode were recorded to illustrate the current density/potential relationship for electropolishing aluminium in zinc (II) nitrate tetrahydrate-choline chloride hydrated salt mixture. The results obtained are shown in Table 5

TABLE 5

Variation of current density with applied potential and the effects on electropolishing.

| Applied voltage V | Current density At Al (mAcm$^{-2}$) | Appearance of Al surface after 5 minutes |
|---|---|---|
| 0 | 0 | no change |
| 1 | 0.2 | " |
| 2 | 1.1 | " |
| 3 | 3.5 | " |
| 4 | 8.8 | " |
| 5 | 17.2 | Smoother and slightly brighter |
| 6 | 27.5 | Smooth and semi-bright |
| 7 | 38.4 | " |
| 8 | 47 | Smooth and 'nearly' bright |
| 9 | 39 | Smooth and very bright |
| 10 | 41.4 | " |
| 11 | 43.4 | " |
| 12 | 45.6 | " |
| 13 | 49 | " |
| 14 | 101 | Etched and bright |
| 15 | 122 | " |
| 16 | 141 | Etched/pitted and semi-bright |
| 17 | 160 | Pitted and semi-bright |
| 18 | 181 | " |
| 20 | 252 | " |
| 22 | 308 | Heavily pitted and dull grey |
| 24 | 343 | " |
| 26 | 423 | " |
| 30 | 1397 | " |

EXAMPLE 56

Stainless Steel Electropolishing

A 2:1 tin (II) chloride dihydrate-choline chloride hydrated salt mixture (~6 ml) was prepared, by the method of Example 1, and poured into an electrochemical cell held in an oil bath at 40° C. To demonstrate stainless steel electropolishing a stainless steel plate (50 mm by 10 mm and 1 mm thick) was cleaned, degreased and fixed to the inside edge of the electrochemical cell. A stainless steel counter-electrode (50 mm by 10 mm and 1 mm thick) was gently abraded with glass paper, cleaned with acetone and flame annealed. The stainless steel counter-electrode was then fixed to the inside edge of the electrochemical cell opposite the stainless steel plate. Electropolishing was achieved by connecting the stainless steel electrodes to the positive and negative terminals of a Thurlby Thander power pack. A potential difference was applied across the 2:1 tin (II) chloride dihydrate-choline chloride electrolyte and adjusted so as to maintain a current density of 65 mAcm$^{-2}$ for 6 minutes at the stainless steel anode. After 6 minutes the anode was removed from the cell, rinsed with acetone and dried. The stainless steel plate was found to be smooth, bright and highly reflective. Scanning electron microscopy was performed and this revealed a highly ordered crystalline surface necessary for good reflectivity and enhanced corrosion resistance.

EXAMPLE 57

Battery

Two hydrated salt mixtures were prepared, 2:1 chromium (III) chloride hexahydrate-choline chloride and 2:1 copper (II) chloride dihydrate-choline chloride at 70° C. 2 ml of each were poured into separated compartments of a small glass cell. The compartments were separated by glass frit. The cell was suspended in an oil bath at 50° C. and zinc and copper strips (2 mm by 30 mm) were immersed in the chromium and copper hydrated salt mixtures respectively. An ISO-TECH IDM66 Digital Voltmeter was used to measure the resulting potential difference—the maximum recorded value was 1.04V.

EXAMPLES 58 to 67

Diels-Alder Reactions

General Procedure for Diels-Alder reactions:

A mixture of diene (0.012 mol) and dienophile (0.012 mol) in $ZnCl_2.2H_2O$:Choline chloride (2:1) (0.5 ml) hydrated salt mixture was stirred (reaction time as given below) and pure cyclo-adduct was separated. For most of the reactions further purification was not necessary but whenever appropriate flash column chromatography was used for further purification. In Examples 54 to 64, "rt" indicates 20° C. For each reaction investigated, the reaction scheme shown was followed employing the procedure as noted in the reference quoted, and NMR chemical shifts (δ) were measured using a 250 MHz instrument.

EXAMPLE 58

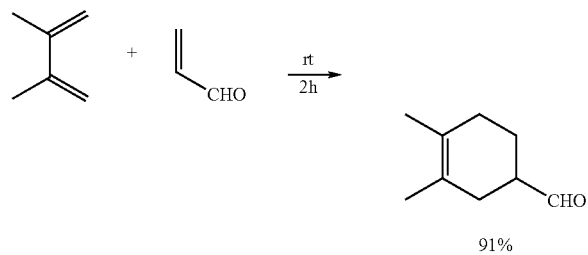

91%

δ 9.67(s, 1H, CHO), 2.46(m, 1H, C*H*CHO), 2.12–1.81(m, 5H, 2×CH$_2$, C*H*H), 1.55(s, 3H, Me), 1.5(s, 3H, Me) and 1.53(m, 1H, C*H*H)

Ref: Odenkirk, W.; Rheingold, A. L.; Bosnich, B., *J. Am. Chem. Soc.*, 1992, 114, 6392

After having separated out the cyclo-adduct and washed the hydrated salt mixture with hexane, the reaction was repeated in the same sample of hydrated salt mixture. The used hydrated salt mixture showed comparable catalytic activity in five subsequent reactions.

EXAMPLE 59

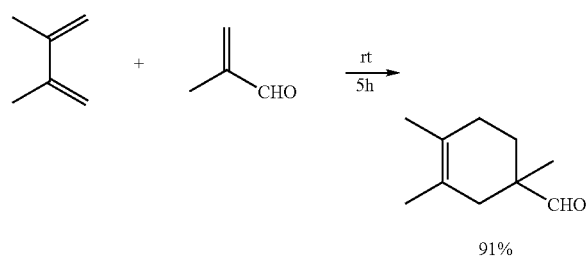

91%

δ 9.46(s, 1H, CHO), 2.25–1.38(m, 6H, 3×CH$_2$), 1.62(s, 3H, Me), 1.58(s, 3H, Me) and 1.01(s, 3H, Me).

Ref: Balwin, J. E. and Lusch, M. J., *J. Org. Chem.*, 1979, 44. 1923.

EXAMPLE 60

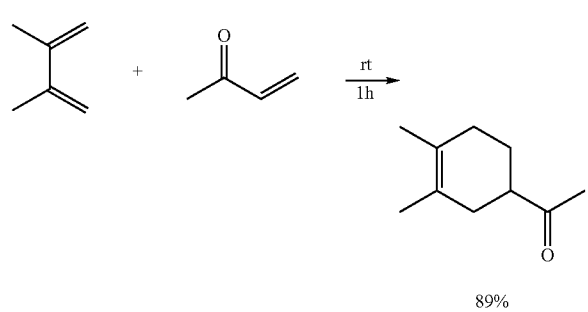

89%

δ 2.55(m, 1H, C*H*Me), 2.18(s, 3H, Me), 2.15–1.84(m, 4H, 2×CH$_2$), 1.57(bs, 6H, 2×Me) and 1.57–1.42(m, 2H, CH$_2$).
Ref: Crabtree, R. H. and Davis, M. H., *J. Org. Chem.*, 1986, 51, 2655.

EXAMPLE 61

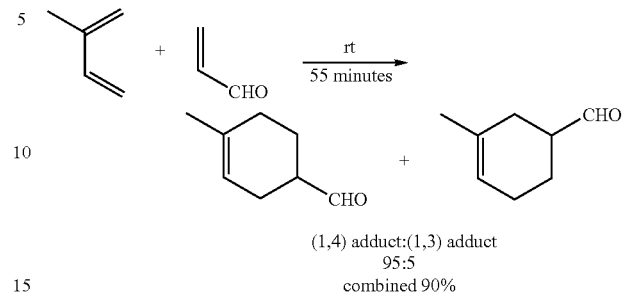

(1,4) adduct:(1,3) adduct
95:5
combined 90%

(1,4) adduct: δ 9.69(d, 1H, J 1.15 Hz, CHO), 5.4(m, 1H, HC═C), 2.46(m, 1H, C*H*CHO), 2.21–1.6(m, 6H, 3×CH2) and 1.65(s, 3H, Me).

Ref: Bonnesen, P. V.; Puckett, C. L.; Honeychuck, R. V. and Hersh, W. H., *J. Am. Chem. Soc.*, 1989, 111, 6070.

EXAMPLE 62

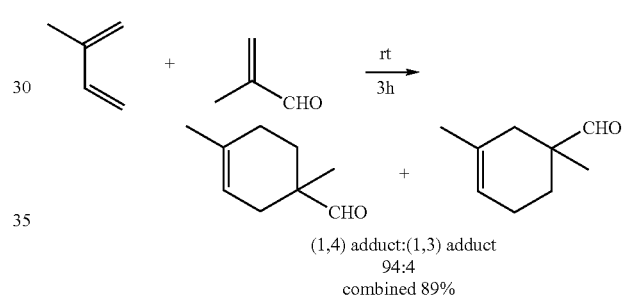

(1,4) adduct:(1,3) adduct
94:4
combined 89%

(1,4) adduct: δ 9.67(s, 1H, CHO), 5.5(bs, 1H, HC═C), 2.6–1.6(m, 6H, 3×CH$_2$), 1.83(s, 3H, Me) and 1.25(s, 3H, Me).

Ref: Balwin, J. E. and Lusch, M. J., *J. Org. Chem.*, 1979, 44. 1923.

EXAMPLE 63

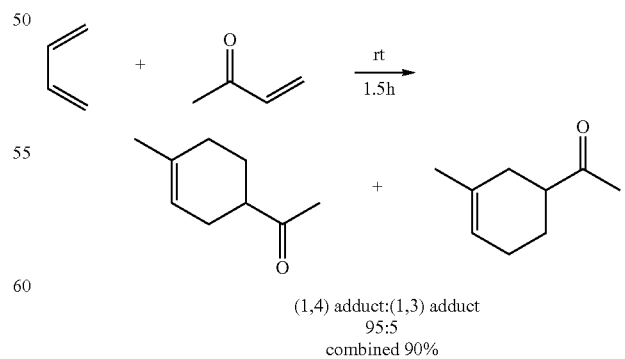

(1,4) adduct:(1,3) adduct
95:5
combined 90%

(1,4) adduct: δ 5.33(bs, 1H, HC═C), 2.54(m, 1H, CHCO), 2.19(s, 3H, Me), 2.19–1.9(m, 4H, 2×CH$_2$), 1.64(s, 3H, Me) and 1.62(m, 2H, CH$_2$).

Ref: Bonnesen, P. V.; Puckett, C. L.; Honeychuck, R. V. and Hersh, W. H., *J. Am. Chem. Soc.,* 1989, 111, 6070.

EXAMPLE 64

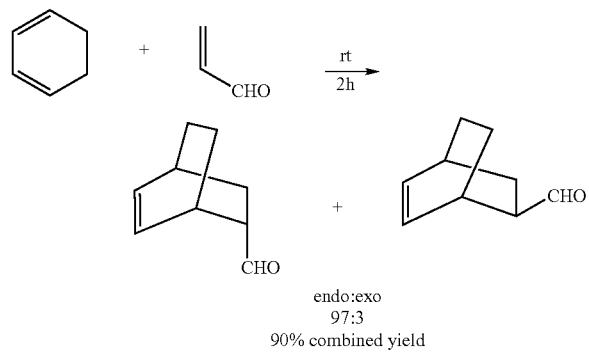

endo:exo
97:3
90% combined yield endo adduct: δ 9.45(d, 1H, J 1.3 Hz, CHO), 6.33(dt, 1H, J 0.9 and 7.5 Hz, HC=C), 6.11(dt, 1H, J 0.9 and 7.5 Hz, HC=C), 2.94(m, 1H, aliphatic-H), 2.65(m, 1H, aliphatic-H), 2.54(m, 1H, aliphatic-H) and 1.7–1.1(m, 6H, aliphatic-H).

Ref: Krantz, A. and Lin, C. Y., *J. Am. Chem. Soc.,* 1973, 95, 5662.

EXAMPLE 65

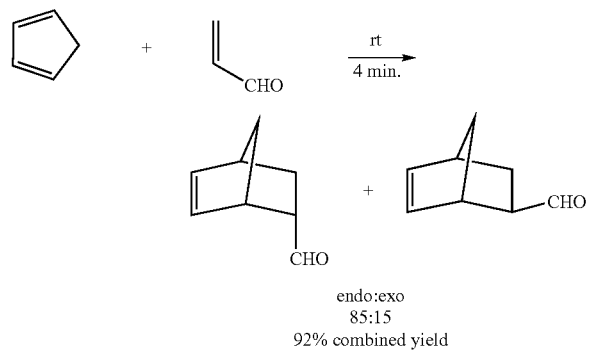

endo:exo
85:15
92% combined yield

Endo adduct: δ 9.42(s, 1H, CHO), 6.18(m, 1H, HC=), 5.96(m, 1H, HC=) and 1.93–1.2(m, 5H, 2×CH₂ and CH) with the peak of exo adduct at δ 9.78(s, 1H, CHO).

Ref: Martin, A.; Reyes, B.; Jose, B. L.; Pedro, C. and Jose, J. L., *Tetrahedron Lett.,* 1998, 39, 2013.

EXAMPLE 66

-continued

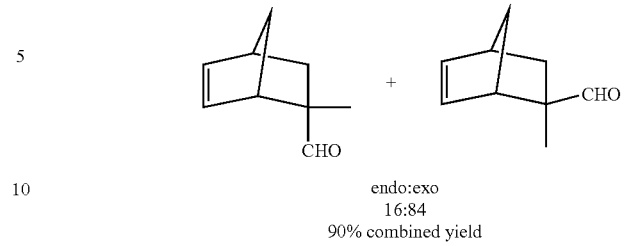

endo:exo
16:84
90% combined yield

Exo adduct: δ 9.67(s, 1H, CHO), 6.3(m, 1H, HC=), 6.08(m, 1H, HC=), 2.26(m, 1H, CH), 2.21(m, 1H, CH), 1.4–1.2(m, 3H, CH₂, CHH), 0.98(s, 3H, Me) and 1.74(d, 1H, J 8.8 Hz, CHH) with the peak of endo adduct at δ 9.38(s, 1H, CHO).

Ref: Narasaka, K.; Inoue, M. and Okada, N., *Chem. Lett.,* 1986, 1109

EXAMPLE 67

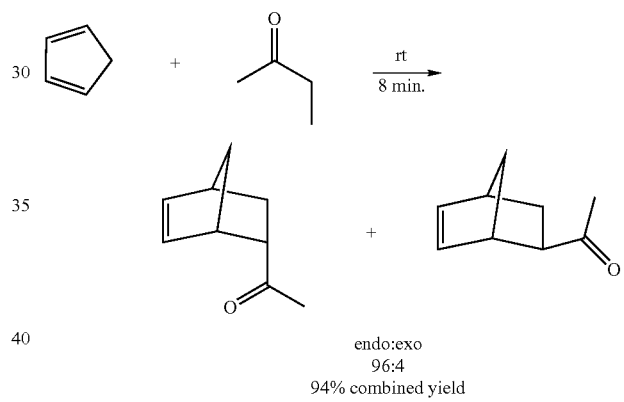

endo:exo
96:4
94% combined yield endo adduct: δ 6.14(m, 1H, HC=), 5.86)m, 1H, HC=), 3.25(bs, 1H, CH), 3.0(m, 1H, HCCHO), 2.88(bs, 1H, CH), 2.1(s, 3H, Me), 1.5–1.4(m, 3H, CH₂ and CHH) and 1.31(d, 1H, J 8.8 Hz, CHH).

Ref: Stork, G and Guthikonda, R. N., *Tetrahedron Lett.,* 1972, 13, 2755.

EXAMPLE 68

Radical polymerisation of a) styrene b) methyl methacrylate in the presence of AIBN catalyst carried out in zinc chloride.2H₂O:choline chloride:water (2:1) ionic liquid under the following conditions.

a)

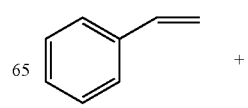

-continued

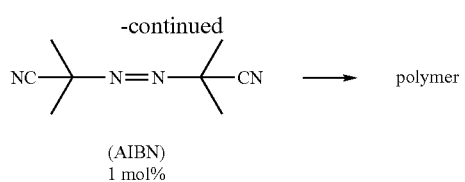

(AIBN)
1 mol%

1. at 80 C, for 4.5 h
2. at 80 C for 16 h b)

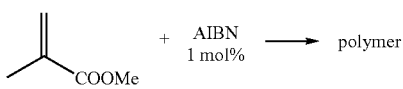

1. at 80 C, for 4.5 h
2. at 80 C for 16 h

The invention claimed is:

1. An ionic compound having a freezing point of no more than 50° C., formed by the reaction of at least one amine salt of the formula

with at least one hydrated salt, which is a chloride, nitrate, sulphate or acetate of Li, Mg, Ca, Cr, Mn, Fe, Co, Ni, Cu, Zn, Cd, Pb, Bi, La, Sn or Ce;

wherein $R^1$, $R^2$ and $R^3$ are each independently a $C_1$ to $C_5$ alkyl or a $C_6$ to $C_{10}$ cycloalkyl group, or wherein $R^2$ and $R^3$ taken together represent a $C_4$ to $C_{10}$ alkylene group, thereby forming with the N atom of formula (I) a 5 to 11 membered heterocyclic ring, and wherein $R^4$ is hydrogen, or phenyl, or a $C_1$ to $C_{12}$ alkyl or cycloalkyl group, optionally substituted with at least one group selected from OH, Cl, Br, F, I, phenyl, $NH_2$, CN, $NO_2$, $COOR^5$, CHO, $COR^5$ and $OR^5$, wherein $R^5$ is a $C_1$ to $C_{10}$ alkyl or cycloalkyl group, and $X_-$ is an anion capable of being complexed by the said hydrated salt.

2. The ionic compound of claim 1, wherein each of $R^1$, $R^2$, $R^3$, independently is a $C_1$ to $C_5$ alkyl or a cycloalkyl group.

3. The ionic compound of claim 2, wherein each of $R^1$, $R^2$, $R^3$, independently is methyl, ethyl or butyl.

4. The ionic compound of claim 3, wherein $R^1$, $R^2$, $R^3$, are each methyl, $R^1$, $R^2$, $R^3$, are each ethyl, or $R^1$, $R^2$, $R^3$, are each butyl.

5. The ionic compound of claim 4, wherein $R^1$, $R^2$, $R^3$, and $R^4$, are each ethyl.

6. The ionic compound of claim 4, wherein $R^1$, $R^2$, $R_3$, are each ethyl, and $R^4$ is hydrogen.

7. The ionic compound of claim 1, wherein $R^4$ is a $C_1$ to $C_{10}$ alkyl or a cycloalkyl group, substituted with at least one group selected from OH, Cl, Br, F, I, phenyl, $NH_2$, CN, $NO_2$, $COOR^5$, CHO, $COR^5$ and $OR^5$.

8. The ionic compound of claim 7, wherein $R^1$, $R^2$, $R^3$, are each methyl, and $R^4$ is 2-hydroxyethyl.

9. The ionic compound of claim 7, wherein $R^1$, $R^2$, $R^3$, are each methyl, and $R^4$ is benzyl.

10. The ionic compound of claim 1, wherein $X^-$ is $Cl^-$ or $Br^-$.

11. The ionic compound of claim 1, wherein the hydrated salt is $ZnCl_2.2H_2O$, $CaCl_2.6H_2O$, $MgCl_2.6H_2O$, $CrCl_3.6H_2O$, $CoCl_2.6H_2O$, $LaCl_3.6H_2O$ $CuCl_2.2H_2O$, $LiCl.5H_2O$, $Ca(NO_3)_2.4H_2O$, $Cr(NO_3)_3.9H_2O$, $Mn(NO_3)_2.4H_2O$, $Fe(NO_3)_3.9H_2O$, $Co(NO_3)_2.6H_2O$, $Ni(NO_3)_2.6H_2O$, $Cu(NO_3)_2.3H_2O$, $Li(NO_3).H_2O$, $Mg(NO_3)_2.6H_2O$, $La(NO_3)_3.6H_2O$, $Cd(NO_3)_2.4H_2O$, $Ce(NO_3)_3.6H_2O$, $Bi(NO_3)_3.5H_2O$, $Zn(NO_3)_2.4H_2O$, $Cd(OAc)_2.2H_2O$, $Pb(OAc)_2.3H_2O$, $SnCl_2. 2H_2O$ or $Cr_2(SO_4)_3.15H_2O$).

12. The ionic compound of claim 1, wherein the ionic compound is formed by reacting the amine salt and the hydrated salt in a molar ratio of from 1:1 to 1:2.5.

13. A method for preparing an ionic compound, which method comprises reacting at least one amine salt of the formula

with at least one hydrated salt, which is a chloride, nitrate, sulphate or acetate of Li, Mg, Ca, Cr, Mn, Fe, Co, Ni, Cu, Zn, Cd, Pb, Bi, La Sn or Ce;

wherein $R^1$, $R^2$ and $R^3$ are each independently a $C_1$ to $C_5$ alkyl or a $C_6$ to $C_{10}$ cycloalkyl group, or wherein $R^2$ and $R^3$ taken together represent a $C_4$ to $C_{10}$ alkylene group, thereby forming with the N atom of formula (I) a 5 to 11 membered heterocyclic ring, and wherein $R^4$ is hydrogen, or phenyl, or a $C_1$ to $C_{12}$ alkyl or cycloalkyl group, optionally substituted with at least one group selected from OH, Cl, Br, F, I, phenyl, $NH_2$, CN, $NO_2$, $COOR^5$, CHO, $COR^5$ and $OR^5$, wherein $R^5$ is a $C_1$ to $C_{10}$ alkyl or cycloalkyl group, and $X_-$ is an anion capable of being complexed by the said hydrated salt.

14. The method of claim 13, further comprising heating the amine salt of the formula (I) with the said hydrated salt.

15. The method of claim 13, further comprising reacting said amine salt and said hydrated salt in a molar ratio of from 1:1 to 1:2.5.

16. A method of carrying out an electrolytic reaction, which method comprises employing as a solvent for the electrolytic reaction the ionic compound of claim 1.

17. The method of claim 16, wherein the electrolytic reaction is an electroplating or an electropolishing reaction.

18. A method of forming a solution of a solute, which method comprises dissolving the solute in an ionic compound having a freezing point of no more than 50° C., formed by the reaction of at least one amine salt of the formula

with at least one hydrated salt, which is a chloride, nitrate, sulphate or acetate of Li, Mg, Ca, Cr, Mn, Fe, Co, Ni, Cu, Zn, Cd, Pb, Bi, La Sn or Ce;

wherein $R^1$, $R^2$ and $R^3$ are each independently a $C_1$ to $C_5$ alkyl or a $C_6$ to $C_{10}$ cycloalkyl group, or wherein $R^2$ and $R^3$ taken together represent a $C_4$ to $C_{10}$ alkylene group, thereby forming with the N atom of formula (I) a 5 to 11 membered heterocyclic ring, and wherein $R^4$ is hydrogen, or phenyl, or a $C_1$ to $C_{12}$ alkyl or cycloalkyl group, optionally substituted with at least one group selected from OH, Cl, Br, F, I, phenyl, $NH_2$, CN, $NO_2$, $COOR^5$, CHO, $COR^5$ and $OR^5$, wherein $R^5$ is a $C_1$ to $C_{10}$ alkyl or cycloalkyl group, and $X_-$ is an anion capable of being complexed by the said hydrated salt.

* * * * *

UNITED STATES PATENT AND TRADEMARK OFFICE
CERTIFICATE OF CORRECTION

PATENT NO.       : 7,196,221 B2                                              Page 1 of 1
APPLICATION NO.  : 10/381059
DATED            : March 27, 2007
INVENTOR(S)      : Andrew P. Abbot et al.

It is certified that error appears in the above-identified patent and that said Letters Patent is hereby corrected as shown below:

In claim 1, line 18, replace "$X\_$" with --$X^-$--

In claim 6, line 1, replace "$R_3$" with --$R^3$--

In claim 13, line 4, replace "$R^1R^2R^3R^4N^+X\_$" with --$R^1R^2R^3R^4N^+X^-$--
line 18, replace "$X\_$" with --$X^-$--

In claim 18, line 6, replace "$R^1R^2R^3R^4N^+X\_$" with --$R^1R^2R^3R^4N^+X^-$--
line 20, replace "$X\_$" with --$X^-$--

Signed and Sealed this

Fourth Day of March, 2008

JON W. DUDAS
*Director of the United States Patent and Trademark Office*